United States Patent [19]

Essen-Moller

[11] Patent Number: 5,477,860
[45] Date of Patent: Dec. 26, 1995

[54] CATHETER FOR MEASURING RESPIRATION AND RESPIRATORY EFFORT

[75] Inventor: Anders Essen-Moller, Stockholm, Sweden

[73] Assignee: Synectics Medical, Inc., Irving, Tex.

[21] Appl. No.: 972,208

[22] Filed: Nov. 5, 1992

[51] Int. Cl.$^6$ .................................................. A61B 5/08
[52] U.S. Cl. .................................................. 128/716
[58] Field of Search ................................. 128/635, 716, 128/719, 725, 748, 760, 207.14, 207.15, 207.18, 204.23

[56] References Cited

U.S. PATENT DOCUMENTS

| | | |
|---|---|---|
| 2,162,656 | 6/1939 | Warrington . |
| 2,168,867 | 8/1939 | George, 3rd . |
| 2,857,915 | 10/1958 | Sheridan . |

(List continued on next page.)

FOREIGN PATENT DOCUMENTS

| | | |
|---|---|---|
| 0073558 | 3/1983 | European Pat. Off. . |
| 0080680 | 6/1983 | European Pat. Off. . |
| 0241644 | 10/1987 | European Pat. Off. . |
| 0356603 | 11/1993 | European Pat. Off. . |
| 2162656 | 12/1971 | Germany . |
| 2453630 | 11/1980 | Germany . |
| 3140265 | 4/1983 | Germany . |
| 211635 | 5/1985 | Germany . |
| 3523987 | 1/1987 | Germany . |
| 7707275 | 1/1979 | Netherlands . |
| 178028 | 11/1966 | U.S.S.R. . |
| 272477 | 8/1970 | U.S.S.R. . |
| 1502004 | 8/1989 | U.S.S.R. . |

OTHER PUBLICATIONS

"Clinical relevance of ambulatory 24–hour. . . ", Vogten, et al., 1987, pp. 21–31 in Netherlands Journal of Medicine.
"Computerized Axial Manometry of the Esophagus", Bombeck, et al. in Annals of Surgery, vol. 206, No. 4, pp. 465–472, Oct. 1987.
"The laser motility sensor for long–term study of intraesophageal pressure", Schneider et al., in Primary Motility Disorder of the Esophagus, Giuli et al., eds., pp. 64–69 1991.
Assorted promotional material by Synetics Medical, Inc.
Kim et al., American Journal of Clinical Pathology, 1990, vol. 94, pp. 187–191, "The Gastric Juice Urea and Ammonia . . . ".
Butcher et al., Digestion, 1992, vol. 53, pp. 142–148, "Use of an Ammonia Electrode for Rapid Quantification of Helicobacter pylori Urease: Its use in the Endoscopy Room and in the . . . ".

(List continued on next page.)

Primary Examiner—Angela D. Sykes
Assistant Examiner—Samuel Gilbert
Attorney, Agent, or Firm—Stephen C. Glazier

[57] ABSTRACT

A catheter for the ambulatory monitoring and recording of respiration, respiratory effort, and pH, to facilitate the study of sleep apnea and related diseases, comprising a tubular body, with one or more lumens, each lumen used for measuring one factor, the possible factors including respiration, respiratory effort, and pH. The tubular body is shown with lumens for monitoring respiration and respiratory effort, each lumen having an opening in the side of the catheter at the site of monitoring. The air in each lumen pneumatically communicates from said opening through the lumen to the proximal end of the catheter. Each air lumen ends in a lead with a connector to which an external pressure sensor can be connected so that said pressure sensor thereby pneumatically communicates with said openings on the catheter. A pH sensor in the catheter has a head portion included in the tubular body and an electrical conductor connected to and extending from the head portion to the proximal end of the tubular body. The electrical conductor is connected with a pH monitor recorder. A method is described for locating obstructions in the respiratory track. A method is described for monitoring and recording on an ambulatory recorder, respiration, respiratory effort, and pH through at least one nightly sleep cycle.

6 Claims, 2 Drawing Sheets

U.S. PATENT DOCUMENTS

| | | | |
|---|---|---|---|
| 3,373,735 | 3/1968 | Gallagher . | |
| 3,480,003 | 11/1969 | Crites | 128/780 |
| 3,669,095 | 6/1972 | Kobayashi et al. . | |
| 3,690,309 | 9/1972 | Pluzhnikov et al. . | |
| 3,817,241 | 6/1974 | Grausz . | |
| 3,905,889 | 9/1975 | Macur et al. . | |
| 3,923,626 | 12/1975 | Niedrach et al. . | |
| 4,016,866 | 4/1977 | Lawton . | |
| 4,063,548 | 12/1977 | Klatt et al. . | |
| 4,073,287 | 2/1978 | Bradley et al. . | |
| 4,119,498 | 10/1978 | Edwall et al. . | |
| 4,176,659 | 12/1979 | Rolfe | 128/635 |
| 4,197,852 | 4/1980 | Schindler et al. . | |
| 4,208,588 | 6/1980 | Rudin . | |
| 4,214,593 | 7/1980 | Imbruce et al. | 128/780 X |
| 4,265,249 | 5/1981 | Schindler et al. . | |
| 4,299,929 | 11/1981 | Sakano et al. . | |
| 4,381,011 | 4/1983 | Somers, 3rd | 128/635 |
| 4,442,841 | 4/1984 | Uehara et al. . | |
| 4,471,779 | 9/1984 | Antoshkiw et al. . | |
| 4,476,871 | 10/1984 | Hon . | |
| 4,478,222 | 10/1984 | Koning et al. . | |
| 4,486,290 | 12/1984 | Cahalan et al. . | |
| 4,487,206 | 12/1984 | Aagard . | |
| 4,503,859 | 3/1985 | Petty et al. | 128/635 |
| 4,508,103 | 4/1985 | Calisi . | |
| 4,577,640 | 3/1986 | Hofmeister . | |
| 4,593,701 | 6/1986 | Kobayashi et al. . | |
| 4,600,015 | 7/1986 | Evans et al. . | |
| 4,618,929 | 10/1986 | Miller et al. . | |
| 4,630,606 | 12/1986 | Weerda et al. | 128/207.14 |
| 4,631,061 | 12/1986 | Martin . | |
| 4,632,119 | 12/1986 | Reichstein . | |
| 4,642,104 | 2/1987 | Sakamoto et al. . | |
| 4,655,225 | 4/1987 | Dahne et al. . | |
| 4,672,974 | 6/1987 | Lee | 128/673 |
| 4,681,116 | 7/1987 | Settler | 128/635 |
| 4,682,596 | 7/1987 | Bales et al. . | |
| 4,691,708 | 9/1987 | Kane . | |
| 4,696,672 | 9/1987 | Mochizuki et al. . | |
| 4,700,709 | 10/1987 | Kraig . | |
| 4,703,757 | 11/1987 | Cohen . | |
| 4,705,503 | 11/1987 | Dorman et al. . | |
| 4,729,384 | 3/1988 | Bazenet . | |
| 4,748,113 | 5/1988 | Marshall . | |
| 4,748,562 | 5/1988 | Miller et al. . | |
| 4,757,194 | 7/1988 | Simms . | |
| 4,776,347 | 10/1988 | Matthews . | |
| 4,796,629 | 1/1989 | Grayzel . | |
| 4,803,992 | 2/1989 | Lemelson . | |
| 4,815,471 | 3/1989 | Stobie . | |
| 4,834,101 | 5/1989 | Collison et al. . | |
| 4,850,371 | 7/1989 | Broadhurst et al. | 128/719 |
| 4,873,990 | 10/1989 | Holmes et al. . | |
| 4,887,610 | 12/1989 | Mittal . | |
| 4,892,101 | 1/1990 | Cheung et al. . | |
| 4,924,877 | 5/1990 | Brooks . | |
| 4,966,161 | 10/1990 | Wallace et al. | 128/748 |
| 4,975,581 | 12/1990 | Robinson et al. . | |
| 4,976,265 | 12/1990 | Falcial et al. . | |
| 4,981,470 | 1/1991 | Bombeck, IV | 128/635 |
| 4,986,671 | 1/1991 | Sun et al. . | |
| 4,991,590 | 2/1991 | Shi . | |
| 4,996,161 | 2/1991 | Conners et al. . | |
| 5,005,584 | 4/1991 | Little . | |
| 5,007,427 | 4/1991 | Suzuki et al. . | |
| 5,022,396 | 6/1991 | Watanabe . | |
| 5,025,786 | 6/1991 | Siegel . | |
| 5,046,497 | 9/1991 | Millar . | |
| 5,047,627 | 9/1991 | Yim et al. . | |
| 5,054,487 | 10/1991 | Clarke . | |
| 5,103,835 | 4/1992 | Yamada et al. . | |
| 5,105,812 | 4/1992 | Corman | 128/780 X |
| 5,108,364 | 4/1992 | Takezawa et al. | 128/748 X |
| 5,117,827 | 6/1992 | Stuebe et al. . | |
| 5,119,498 | 6/1992 | McNeill et al. . | |
| 5,151,598 | 9/1992 | Denen . | |
| 5,158,083 | 10/1992 | Sacristan et al. . | |
| 5,184,619 | 2/1993 | Austin . | |
| 5,199,443 | 4/1993 | Maurer et al. . | |
| 5,207,226 | 5/1993 | Bailin et al. . | |
| 5,222,594 | 6/1993 | Sumino . | |
| 5,280,786 | 1/1994 | Wlodarczyk et al. . | |
| 5,291,884 | 3/1994 | Hienemann et al. . | |
| 5,301,673 | 4/1994 | Rabito et al. . | |
| 5,314,804 | 5/1994 | Boguslaski et al. . | |

OTHER PUBLICATIONS

The New Yorker, Sep. 20, 1993, T. Monmaney, "Marhsall's Hunch".

"Oesophageal multipurpose monitoring probe", Baker et al., Anaesthesia, 1983, vol. 38, pp. 892–897.

World Wide Patent Monocrystant . . . (Brochure).

Digestive Diseases, Reprint, vol. 8, Suppl. 1, pp. 60–70, 1990, Scarpignato et al., "Simultaneous Measurement and Recording . . . ".

Hojgaard et al., "A New Method for Measurement of the Electrical Potential Difference Across the Stomach Wall", 1991. pp. 847–858.

"Ambulatory Monitoring of Gastric Emptying", Hoeft et al., May 16, 1993, American Assoc. of the Study of Live Diseases.

CATHETER FOR MEASURING RESPIRATION AND RESPIRATORY EFFORT

TECHNICAL FIELD

The present invention relates to catheters that monitor respiration and respiratory effort. More particularly, the present invention relates to devices that monitor inhalation pressures with or without pH related to respiration in patients and, specifically, in the study of sleep apnea.

BACKGROUND ART

Catheters are well known in medicine and a wide variety exist for a variety of purposes. Catheters are typically flexible tubes of varying sizes that are inserted into the body. One common application of catheters, for example, is the removal of bodily fluids from the bladder during the time when the patient is incapacitated. As the technology of medicine has expanded, catheters are becoming more widely used for a greater variety of purposes.

Catheters exist that have pressure sensors at the distal tip. When these pressure sensors are inserted into the body, the local pressure around the distal tip of the catheter is able to be measured. In general, these prior art pressure sensors are usually used to measure the pressure of solid body parts against the catheter, and not air pressure in spaces filled with air.

Catheters also exist that have on their distal end a pH sensor. In these types of catheters, an electrical wire runs inside the catheter to the proximal end of the catheter. When the catheter is inserted into the body, this arrangement permits the electrical sensing of pH (that is, acidity) of the immediate environment of the distal tip. Such pH catheters are presently manufactured by Synectics Medical AB of Sweden, distributed in the U.S. by Synectics Medical, Inc. of 1425 Greenway Drive, Suite 600, Irving, Tex.

A lumen is a channel inside the catheter that runs the length of the catheter. Multiple lumen catheters are well known. These catheters can function much like multiple catheters with each lumen dedicated to one function. As such, a single catheter with multiple lumens can operate as a multiple function catheter. Since the diameter of the catheter is of critical importance, it becomes difficult to incorporate a large number of lumens within a single catheter. The restriction of space availability inhibits the ability to incorporate many functions into one catheter.

Several methods are known that attempt to measure the degree of effort a patient is exerting in the attempt to breathe. The degree of effort exerted in the attempt to breathe is identified as "respiratory effort". Such methods include applying stretch sensitive belts (similar to strain gauges) to the outside of the abdomen, or the application of electrodes to the chest to measure changes in impedance. These approaches are cumbersome and inaccurate. The most accurate technique for measuring respiratory effort is through measuring air pressure changes in the esophagus or stomach. An effort to inhale results in an air pressure drop in the esophagus and trachea, and in a pressure increase in the stomach. This happens even though real inspiration and movement of air from the ambient room to the patient's lungs may not necessarily follow due to, for example, pharyngeal obstruction. An effort to exhale causes analogue events, but in the opposite directions (that is, an air pressure increase in the esophagus and trachea, and a drop in the stomach). When no effort to breathe occurs, the air pressure is these areas will remain constant.

The prior art in the area of respiratory effort in the esophagus includes placing a balloon made from the finger of a latex glove on the end of an esophageal catheter. The balloon is then partially inflated. An air pressure monitor at the proximal end of the catheter connected to the balloon indicates respiratory effort. The relatively large size of the balloon often interfered with the esophageal function and other simultaneous intraesophageal catheterizations. Prior art includes using a small balloon fixed to a piece of tubing and connected to an exterior pressure transducer as in U.S. Pat. No. 4,981,470, issued on Jan. 1, 1991 to Bombeck. This design still has the disadvantage that it is relatively large, expensive and difficult to produce. Also this design can only be used to monitor respiratory effort and not actual respiration.

Prior art to monitor respiratory effort also includes the use of a somewhat inflated balloon communicating with a pressure transducer via plastic tubing. The balloon is taped externally onto the stomach so that inspirations and expirations stretch the balloon thereby creating positive and negative pressure fluctuations in the tubing. The tubing communicates with the pressure transducer monitoring respiratory effort, rather than air flow. This method does not measure pressure changes due to movement of air in, or in the proximity of, the lung airways or the esophagus. This method is also less sensitive and more prone to errors due to body movement or badly taped sensors.

Prior art to measure respiration, that is actual movements of air in and out of the respiratory organs such as the nostrils, uses thermistors that monitor the temperature of respiratory air. This is based on the idea that inspiratory air is cooler than expiratory air. Such thermistors are not connected to pressure transducers. Alternatively pneumotachographs exist where two pressure sensors in series monitor pressure drops over a resistor. This is used to calculate air flow and volume, which information is used in turn to calculate peak flow and tidal volumes. This method is however complicated and expensive and introduces "dead space" as it extends the breathing circuit.

Soviet Patent No. 272,477, issued on May 20, 1968 to Leya and Berzinsh, teaches a stomach-intestinal probe consisting of multiple antimony electrodes to measure stomach acids and a large inflatable balloon to fix the probe in the esophagus so that fluoroscopy can be used to watch the movement of the stomach. This probe permits simultaneous monitoring of stomach acid and stomach movements. However, the balloon is relatively large and blocks esophagus function, thus breaking normal sleep patterns. Also, the balloon cannot function as a pressure sensor since it is too large and not connected to an external pressure monitor.

German Patent No. 2,162,656, issued to Wolters and Eckert on Jun. 20, 1973, teaches a stomach acid gauge with an electrical pH sensor. Once again, this device does not measure respiratory effort. Similar one-function stomach acid sensors are taught by U.S. Pat. No. 4,618,929, issued on Oct. 21, 1986 to Miller et al. al. and by U.S. Pat. No. 4,176,659 issued on Dec. 4, 1979 to Rolfe.

U.S. Pat. No. 4,503,859, issued on Mar. 12, 1985, to Petty, et al., teaches a device to simultaneously monitor esophageal acid and heart EKG. This device does not measure respiratory effort in any way.

German Patent No. DE 3523987A, issued on Jan. 8, 1987, to Lange, teaches a method to measure stomach function consisting of multiple pH sensors attached to the outside of a balloon on a catheter. The balloon, however, is used only to inflate inside the stomach and thereby distribute the pH sensors against the stomach wall. Normal esophageal function is blocked, pH in the esophagus is not tested, and respiratory effort is not measured.

U.S. Pat. No. 4,681,116, issued on Jul. 21, 1987, to Settler, teaches an antimony electrode used as an esophageal electrode. This uses an epoxy resin as a sealant. This is also a single function device which does not simultaneously monitor respiratory effort.

Sleep apnea is the problem of inadequate breathing while asleep. It can have several causes, with each cause requiring different remedies. Hence, individual treatment of sleep apnea can follow only after study of the causes of sleep apnea in the individual.

One alternative cause of sleep apnea is gastroesophageal reflux (GER). GER is the process by which the subject generates acids in the stomach, which are then passed into the esophagus. These acids can then be aspirated into the lungs, causing a constriction of the trachea and difficulty in breathing. However, GER can also be a result instead of a cause, of sleep apnea. Difficulty in breathing, caused by other reasons, can lead to increased respiratory effort in compensation. This increased effort can then encourage GER. In effect, this causes a sucking of the gastric acid into the esophagus from the stomach.

Yet other causes of apneas in the sleep apnea syndrome may be of neurological origin or, more often, from obstruction due to the collapse of the posterior pharyngeal wall during inspiration. Such obstruction may be partial and give rise to the snoring sound. In obstruction sleep apnea the patient's respiratory efforts may not result in adequate movement of air into and out of the patient's lungs in spite of adequate respiratory efforts.

Therefore, to determine the cause of an individual's cause of sleep apnea, and to determine the proper remedy, it is necessary in each individual case to study and sort out the cause and effect relationship of GER, respiratory effort, and respiration (movement of air in the upper airways). In practice, this requires the accurate simultaneous measurement of intraesophageal acid, respiratory effort, and respiration. Specifically, this means the accurate simultaneous measurement of pH in the esophagus, air pressure in the esophagus, and air pressure or air flow in the proximity of the mouth and nostrils. It is also important that this should be done in a way that does not disturb normal sleep, and other bed activity. Unfortunately, no techniques have been developed prior to the present invention which measure all of these factors simultaneously. As a result, the effective study and remedy of sleep apnea is not yet available to medical specialists.

It is an object of this invention to provide a catheter that monitors respiratory effort in the upper gastrointestinal tract (the stomach and esophagus) distal to any nasal or pharyngeal obstructions without using a balloon.

It is another object of this invention to provide a catheter that monitors respiration using the same design as for respiratory effort only placing the monitoring site (that is, the inlet to the catheter) proximal to a possible obstruction site.

It is yet another object of this invention to provide a catheter that monitors both respiratory effort and respiration by using tubing with more than one lumen and the technology described above.

It is yet another object of this invention to provide a catheter that can localize nasal or pharyngeal obstructions using one or more lumens in the tubing, or one or more catheters and the technology described above.

It is yet another object of this invention to provide a catheter that is designed according to any of the objects described above and that includes one or more pH measuring points.

It is an object of the present invention to provide a catheter that monitors movements of air by means of a single air pressure transducer inside or in the immediate proximity of the upper airways such as the nostrils (to measure respiration) or in the esophagus (to measure respiratory effort) or both, without the introduction of dead space and with or without a pH sensor included.

It is another object of the present invention to provide such a catheter that can be utilized without disturbing sleep.

It is a further object of the present invention to provide such a catheter that is compatible with fluoroscopy techniques.

It is still a further object of the present invention to provide an instrument that simultaneously monitors gastric reflux, respiratory effort, and respiration.

These and other objects and advantages of the present invention will become apparent from a reading of the attached specification and appended claims.

SUMMARY OF THE INVENTION

The present invention is a catheter that comprises a tubular body, with one or more lumens, each connected to one external pressure transducer for monitoring and recording respiration and/or respiratory effort, and with or without a pH sensor. The external pressure sensor or sensors communicate, via the lumen or lumens through the interior of the tubular body, to sites where pressure is to be monitored. The pH sensor lead extends through the interior of the tubular body and is used for the purpose of detecting acidity within the esophagus or stomach.

The present invention is a catheter for the ambulatory monitoring and recording of respiration, respiratory effort, and pH, to facilitate the study of sleep apnea and related diseases, comprising a tubular body, with one or more lumens, each lumen used for measuring one factor, the possible factors including respiration, respiratory effort, and pH. The tubular body is shown with lumens for monitoring respiration and respiratory effort, each lumen having an opening in the side of the catheter at the site of monitoring. The air in each lumen pneumatically communicates from said opening through the lumen to the proximal end of the catheter. Each air lumen ends in a lead with a connector to which an external pressure sensor can be connected so that said pressure sensor thereby pneumatically communicates with said openings on the catheter. A pH sensor in the catheter has a head portion included in the tubular body and an electrical conductor connected to and extending from the head portion to the proximal end of the tubular body. The electrical conductor is connected with a pH monitor recorder.

The tubular body is comprised of a clear polyvinyl chloride material. This tubular body has a radiopaque stripe that extends for the length of the tubular body. Specifically, this radiopaque stripe is red and is of a type that can easily be seen under fluoroscopy. This radiopaque stripe runs for the entire length of the catheter. The tubular body also has a plurality of circumferential gradations marked on the tubular body. These circumferential gradations are indicative of distance from one end of the tubular body. The tubular body has an outer diameter of 2.1 millimeters. The catheter has one or more lumens which are large enough to accommodate the pH sensor lead and allow air flow to pass therethrough.

The pH sensor comprises a head portion that is fastened at the pH measuring site of the tubular body and an electrical conductor that is connected to the pressure sensor and extends from the head portion to the proximal end of the tubular body. The head portion is pH sensitive. This head portion is made of a polycarbonate material. This head portion should have a smooth, rounded surface having no sharp edges. This head portion is bonded to one end of the tubular body.

The conductor is a coated wire having a connector fastened to the proximal end of the conductor outside of the proximal end of the catheter. This coated wire is specifically TEFLON coated and has a diameter of approximately 0.6 millimeters. This coated wire is fitted within the lumen of the catheter.

At the site or sites where respiration or respiratory efforts will be monitored at the distal end of the catheter, an opening in the side of the catheter for each lumen to be used, which allows each lumen to pneumatically communicate from that point to the proximal end of the lumen. Thus each opening communicates through a lumen acting as an air channel of a diameter of 0.8 millimeters to a pressure transducer at the proximal end of the tubular body. The openings are expanded to prevent occlusion and have an approximate diameter of 1.3 millimeters.

DETAILED DESCRIPTION OF THE INVENTION

Figure 1:
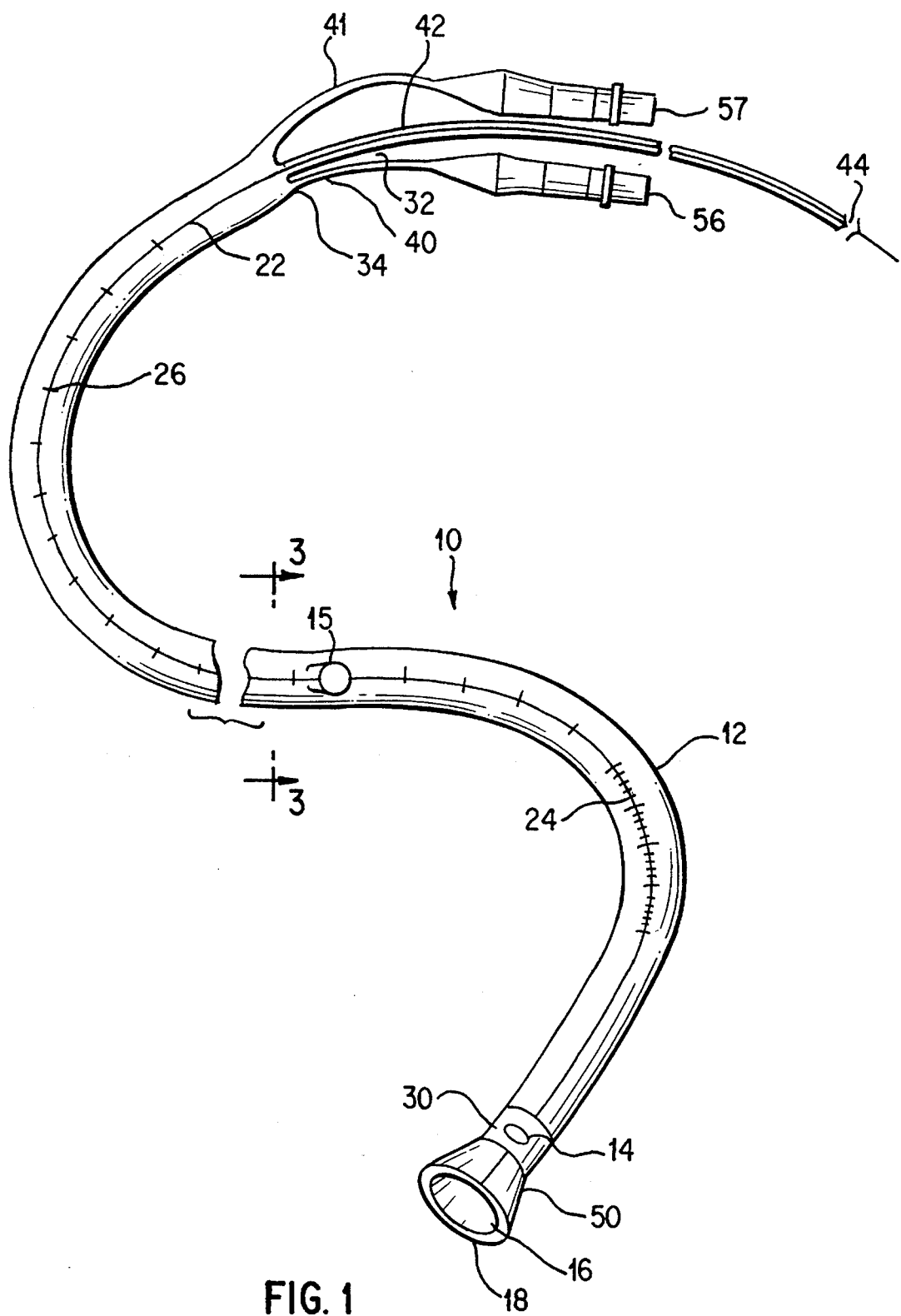
FIG. 1 is a diagrammatic side view of the catheter in accordance with the preferred embodiment of the present invention.

FIG. 1 shows the catheter 10 in accordance with the preferred embodiment of the present invention. Catheter 10 comprises tubular body 12, pH sensor 14, and opening 15 for interior communication with the air pressure monitor and recorder for respiration and opening 16 for interior communication with the air pressure monitor and recorder for respiratory effort. The pH sensor 14 is connected to an electrical conductor that extends through the interior of the tubular body 12 so as to provide for pH measurement close to the distal end 18.

The tubular body 12 of the catheter 10 is a three lumen catheter having an outer diameter of approximately 2.1 millimeters. The tubular body 12 is comprised of a clear polyvinyl chloride (PVC) material. The interior surfaces of the lumens are lined with TEFLON. The tubular body 12 includes a red radiopaque stripe 22 extending longitudinally for the entire length of catheter 10. This radiopaque stripe 22 should be of a type that can be easily seen during fluoroscopy.

The tubular body 12 is marked circumferentially with gradations 24. In the preferred embodiment, these gradations occur in one centimeter increments. All of these markings are relative to the distance from the distal tip 18 of the catheter 10. Every fifth circumferential mark has a slightly thicker band 26 and is appropriately numbered. The markings and numberings start at the five centimeter mark from the distal tip 18 and proceed approximately to forty centimeters. These markings allow the use of the catheter 10 to appropriately position the catheter within the body of the patient and to make approximations as to the location of the catheter within the body.

The pH sensor 14 comprises a head portion 30 that is inserted in the catheter close to the distal end of the tubular body 12. The pH sensor further comprises a conductor 32 that is connected to the head portion 30 and extends from the head portion 30 to the proximal end 34 of the tubular body. The head portion 30 is of a polycarbonate material having a smooth surface. The pH sensor of the present invention is a monocrystant antimony pH sensor. The head portion 30 is of the same diameter as the tubular body 12 so that there are no sharp edges. A longitudinal hole in the head portion 10 allows free communication of pressure changes through the lumen that measures respiratory effort from said hole in the head portion 30 to the proximal end 56 of the same lumen. The head portion 30 is fixed in place in the tubular body 12 by ultrasonic or vibration bonding. The head portion 30 and the widening end piece 50 have an interior channel connecting the opening 16 to a lumen to provide a continuous air channel from opening 16 to the proximal end of the catheter.

The pH sensor 14 and the opening for monitoring of respiratory effort 16 should be installed in such a way that the pH sensor 14 and said opening 16 remain separated. Ideally, this separation should be at least three centimeters. The reason for this separation is to allow the esophagus ample room to contract around the catheter body, and clear residual GER away from the pH sensor.

The tubular body 12 should have a length of approximately fifty centimeters. The proximal end 34 of the catheter 10 should be broken out into three clear polyvinyl chloride leads 40, 41 and 42. The pH sensor channel lead 42 should have a length of approximately seventy centimeters and an inner diameter of 0.9 millimeters. The pH portion of the catheter 10 will thus have an overall length around one hundred and twenty centimeters. The conductor 32 for the pH sensor 14 should be TEFLON coated. This conductor 32 is to be threaded through the pH sensor lumen of the catheter 10, through the pH channel lead, and terminated with a male tip plug connector 44. The pH sensor conductor 32 is secured to plug 44. Plug 44 may then be connected to an appropriate monitor for monitoring acidity conditions within the esophagus.

The opening 16 for the respiratory effort comprises a widening 50 of the catheter that is molded onto the tubular body 12. In addition, said opening 16 for respiratory effort leads to an air pressure communication lumen that extends through the interior of the tubular body 12 and the head portion 30 such that said lumen communicates through opening 16 to lead 40.

As will be described hereinafter, the air pressure communication lumens 40 and 41 are TEFLON-lined. The lumen leads 40 and 41 are connected to plugs 56 and 57 that may be attached to an adjacent air pressure monitor and recorder, external to the catheter. The lumen leads 40 and 41 should have a length of 20 centimeters and an inner diameter of approximately 0.9 millimeters. The channel leads 40 should be made of TEFLON and have a cross-sectional configuration such that the leads 40 and 41 will not kink. The leads 40 and 41 are terminated with female luer locks 56 and 57. The ports or openings 16 and 15 are widened to about 1.3 millimeters to prevent clogging in the catheter.

Figure 2:
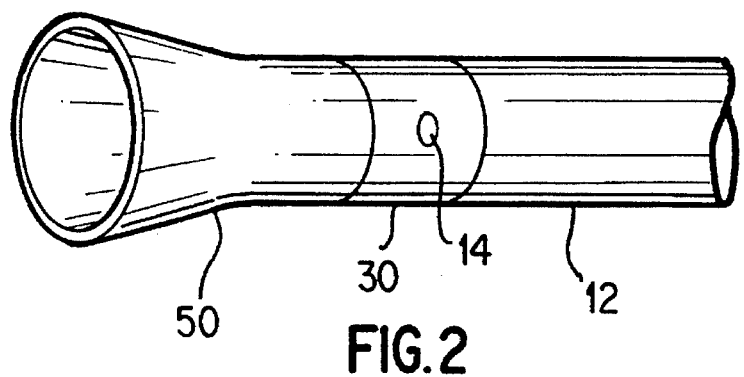
FIG. 2 is an end view of the catheter of the present invention.

Referring to FIG. 2, there is shown an end view of the catheter 10. Specifically, in this end view, there is shown the widening end piece 50 of the catheter that is mounted on head portion 30. The head portion 30 is of a polycarbonate material. The electrical conductor (not shown) from the pH sensor is inside of the head portion 30, and is connected to the end of the pH sensor 14. The tubular body 12 is attached to the head portion 30 which in turn is attached to the widening end piece 50 of the catheter by ultrasonic or vibration bonding. Since the instrument of the present invention is to be used in internal medicine, it is important to avoid adhesives and other bonding agents.

Figure 3:
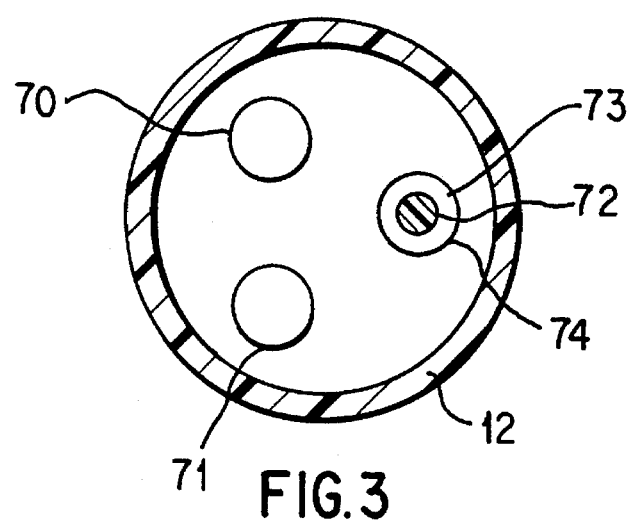
FIG. 3 is a cross-sectional view taken along lines 3—3 of FIG. 1 of the present invention.
Figure 4:
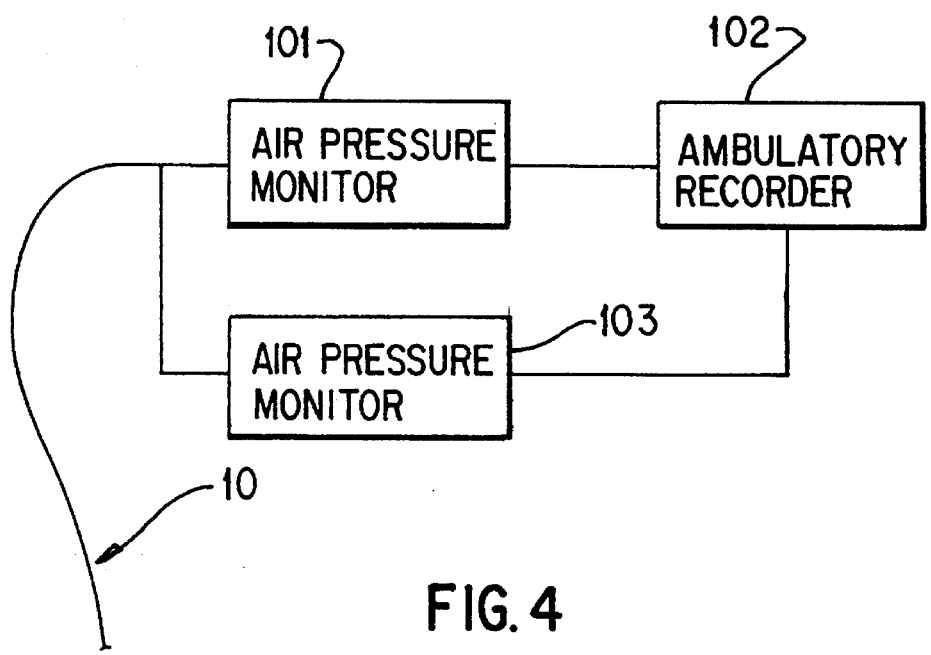
FIG. 4 shows the catheter of the present invention attached to two air pressure monitors, which are attached to an ambulatory recorder.

FIG. 3 shows a cross-section view of the internal configuration of catheter 10 proximal to the opening 15 that communicates with the pressure sensor for monitoring of respiration via lead 41. There are three lumens 70, 71 and 73. Lumen 73 contains the conductor 72 for the pH sensor 14 (shown in FIG. 1). Conductor 72 is coated with TEFLON material 74. This TEFLON-coating allows the conductor to be easily threaded through the lumen 73 within the catheter 10. This conductor is threaded through the lumen 73 of the catheter 10, through the pH lumen lead 42 (as shown in FIG. 1) and eventually terminates with plug 44 (see FIG. 1). The lumen 73 (the pH sensor channel) must be large enough to accommodate the TEFLON coated wire 72. Lumens 70 and 71 should have a diameter of 0.9 mm to allow adequate air flow communication from openings 15 and 16 through said lumens 70 and 71 to channel ends at connectors 56 and 57. The walls of channel lumens 70 and 71 should be TEFLON-lined in order to increase resistance to radial deformation and to reduce air flow resistance. FIG. 3 also shows the inclusion of the red radiopaque stripe 22 as formed on the clear polyvinyl chloride tubular body 12.

In operation as a single lumen variation, the distal end opening 16 on catheter 10, without opening 15 and without pH sensor 14, communicates with the lumen's proximal end, where an air pressure sensor is connected to the air channel lumen communicating with opening 16 to monitor respiratory effort or respiration. When the catheter is properly placed in the esophagus (where negative pressure is created during an inspiratory effort) and positive pressure is created during an expiratory effort it is possible to monitor respiratory effort and its direction (respiratory or inspiratory). If on the other hand opening 16 (or if a two channel catheter is used, opening 15), is placed in proximity of the nostrils, movement of air is measured with this lumen, and actual respiration (or inspiration) is measured. In a two lumen variation, opening 15 communicates through a lumen separate from opening 16, to a separate air pressure monitor and recorder. If, in the case of a two lumen probe, opening 16 is placed distal to a nasopharyngeal obstruction and opening 15 is placed proximal thereto, then lack of a respiration signal in the presence of a respiratory effort signal indicates said obstruction.

With a pH sensor attached, it is possible to correlate apneas and respiratory efforts with GER. This can be done by simultaneously measurement of three factors (GER, respiration, and respiratory effort), with one catheter.

A method of using the apparatus of the present invention to determine the existence and location of an obstruction in the respiratory track comprises the steps of (a) introducing a first catheter with a distal opening from an internal lumen which proximal end is connected to an external pressure transducer and monitor so that said distal opening is positioned distal to the obstruction thus monitoring respiratory effort, (b) positioning a second catheter of similar type as above or of thermistor type so that the sensing site is just inside or in the neighborhood of the nostrils thus monitoring actual respiration, and (c) verifying the existence of an obstruction by observing respiratory effort signals without corresponding respiration signals.

This method can further comprise (a) locating the obstruction by inserting the second catheter monitoring respiration deeper into the respiratory track until respiration signals similar to the respiratory effort signals cease to occur, indicating that the second catheter now also has been pushed over to the distal side of said obstruction.

Alternatively, this method can further comprise (a) locating the obstruction by withdrawing the first catheter until it registers respiration effort signals similar to the respiration signals of the second catheter, indicating that the first catheter has then crossed over to the proximal side of said obstruction.

As yet another alternative of this method, the role of the first and second catheter are performed by a first and second lumens in one catheter, with a spacing along the length of the catheter between the distal openings of the first and second lumens.

Another method of using the apparatus of the present invention, this one for ambulatory monitoring and recording of respiration and respiratory effort, comprises the steps of (a) introducing into the respiratory track a catheter with a number of air communication channels extending through such catheter, with one distal opening for each such channel, each opening pneumatically communicating with an ambulatory air pressure monitor external to the patient, and (b) recording on an ambulatory recorder external to the patient the air pressure measurements from each such opening, corresponding to respiration and respiratory effort, for a period including one nightly sleep cycle of the patient. This method may further comprise the steps of (a) introducing a catheter with a pH sensor means electrically communicating through the catheter to the ambulatory recorder external to the patient, and (b) recording on such ambulatory external recorder the pH measurements from such pH sensor, over a period including one night sleep cycle of the patient.

In the study of sleep apnea, the present invention allows the measurement of one or more of the parameters of respiration, respiratory effort, and pH, including their interrelationships. The present invention allows these measurements to be taken simultaneously and when desired with the use of a single catheter. The catheter of the present invention is of such a small diameter that it does not disturb normal sleep or other bed activity. As such, the present invention allows the effective study and analysis of sleep apnea that has until now eluded medical science.

The embodiment illustrated and discussed in the specification is intended only to teach to those skilled in the art the best way known by the inventor to make and use the invention. Nothing in the specification should be considered as limiting the scope of the present invention. Changes could be made by those skilled in the art to produce equivalent systems without departing from the invention. The present invention should only be limited by the following claims and their legal equivalents.

For example, any combination of air pressure opening sites (one, two or more) with a pH or other sensor may be used. Also, the distance from opening 16 to opening 15, and the relative placement of the pressure sensor may be varied to accommodate particular requirements. Also, the resulting information regarding pressure and pH may be monitored, recorded, processed and displayed in different manners once collected by the catheter.

I claim:

1. A method of determining existence and location of an obstruction in a respiratory track comprising the steps of:

(a) introducing a first catheter with a distal opening from an internal lumen having a proximal end connected to an external pressure transducer and monitor so that said distal opening is positioned distal to the obstruction, using the first catheter to monitor respiratory effort and generating signals indicative of respiratory effort;

(b) positioning a second catheter so that a sensing site is sufficiently near nostrils, using the second catheter to monitor actual respiration and generating signals indicative of actual respiration; and (c) verifying existence of the obstruction by observing respiratory effort signals without corresponding respiration signals.

2. A method as defined by claim 1, further comprising the step of locating the obstruction by inserting the second catheter into the respiratory track until the signals indicative of actual respiration cease to occur, indicating that the second catheter also has been pushed to a distal side of said obstruction.

3. A method as defined by claim 1, further comprising the step of locating the obstruction by withdrawing the first catheter until it registers respiration effort signals similar to respiration signals registered by the second catheter, indicating that the first catheter has crossed over to a proximal side of said obstruction.

4. A method as defined by claim 1, wherein said second catheter is similar to said first catheter.

5. A method as defined by claim 1, wherein said second catheter is of a thermistor type.

6. A method as defined by claim 1, wherein the step of positioning said second catheter includes positioning said second catheter just inside one of the nostrils.

* * * * *